United States Patent [19]
Chattopadhyay et al.

[11] Patent Number: 5,856,532
[45] Date of Patent: Jan. 5, 1999

[54] PROCESS FOR THE PRODUCTION OF TAXOL

[75] Inventors: Sunil Kumar Chattopadhyay; Ram Prakash Sharma; Sushil Kumar; Kunnath Padmanabhan Madhusudanan, all of Lucknow, India

[73] Assignee: Council of Scientific & Industrial Research, New Dehli, India

[21] Appl. No.: 909,810

[22] Filed: Aug. 12, 1997

[30] Foreign Application Priority Data

Aug. 14, 1996 [IN] India .......................... 1803 DEL 1996

[51] Int. Cl.$^6$ ................................................ C07D 305/14
[52] U.S. Cl. .......................................... 549/510; 549/511
[58] Field of Search ...................... 549/510, 511

[56] References Cited

U.S. PATENT DOCUMENTS 5,200,534  4/1993  Rao .......................................... 549/510
5,367,086  11/1994  Rao .......................................... 549/510

OTHER PUBLICATIONS

Senilh, V., Blechert, S., Colin, M., Guenard, D., Picot, F., Potier, P. and Varenne, P. "Mise en Evidence de Nouveaux Analogues du Taxol Extraits de Taxus baccata", *Journal of Natural Products,*vol. 47, no. 1, pp. 131–137, 1984.

Miller, Roger W., Powell, Richard G., Smith, Cecil R. Jr., "Antileukemic Alkaloids from Taxus wallichiana Zucc.", *The Journal of Organic Chemistry,*vol. 46, No. 7, pp. 1469–1474, 1981.

Barboni, Luciano, Gariboldi, Pierluigi, Torregiani, Elisabetta, Appendino, Giovanni, Gabetta, Bruno and Bombardelli, Ezio, "Taxol Analogues from the Roots of Taxus Media", *Phytochemistry, The International Journal of Plant Biochemistry,*vol. 36, No. 4, pp. 987–990, 1994.

Ma, Wenwen, Park, Gary L., Gomex, George A., Nieder, Matthew H., Adams, Tom L., Aynsley, John S., Sahai, Om P., Smith, Richard J., Stahlhut, Roy W., and Hylands, Peter J., "New Bioactive Taxoids from Cell Cultures of Taxus Baccata", *Journal of Natural Products,*vol. 57, No. 1, pp. 116–122, 1994.

Wani, M.C., Taylor, H.L., Wall, Monroe E., Coggon, P., McPhail, A.T., "Plant Antitumor Agents. VI. The Isolation and Structure of Taxol, a Novel Antileukemic and Antitumor Agent from *Taxus brevifolia*", *Journal of the American Chemical Society,*vol. 93, No. 9, pp. 2325–2327, 1971.

Cardellina, John H., II, "HPLC Separation of Taxol and Cephalomannine", *Journal of Liquid Chromatography,*vol 14, No. 4, pp. 659–665, 1991.

Chattopadhyay, Sunil K., Kulshrestha, Manish, Saha, Gour C.., Sharma, Ram P., Jain, Shital P., and Kuman, Sushil, "The Taxoid Constituents of the Heartwood of Taxus wallichiana", *Plant Medica,*vol. 62, p. 482, 1996.

Chattopadhyay, S.K., Tripathi, V.K., Thakur, R.S., Sharma, R.P., and Jain, S.P., Isolation of Taxol, 10–deacetylbaccatin III and (–)–betuligenol from Taxus baccata, *Indian Journal of Chemistry*, vol. 33B. pp. 409–411, 1994.

*Primary Examiner*—Ba K. Trinh
*Attorney, Agent, or Firm*—Merchant, Gould, Smith, Edell, Welter & Schmidt

[57] ABSTRACT

A process has been developed for production of taxols A, B, C with high yields from 7-xylosyl-10-deacetyl taxol A (taxol analogue A or, xyloside A), 7-xylosyl-10-deacetyl-taxol B (taxol analogue B or xyloside B), 7-xylosyl-10-deacetyl—taxol C (taxol analogue C or xyloside C), which comprises (i) isolating the taxol analogues A, B, C form the stembark of *Taxus wallichiana* by an improved process devoiding of solvent partitioning step, (ii) treating the isolated taxol analogues A, B, C with periodates in an acid free polar solvent medium to cleave the diol into dialdehyde at ambient temperature, (iii) reducing the dialdehyde solution with borohydride in a polar solvent—acetic acid medium at 0°–40° C. into an acetal, (iv) acidifying the resultant acetal with a mixture of mineral acid-polar solvent at 0°–40° C. into intermediate product 10-deacetyl taxols A, B, C, (V) reacting 10-deacetyl taxols A or B or C with a silane in presence of a base at 20°–40° C. to protect 2', 7-hydroxyl groups, of 10-deacetyl taxols A, B, C (vi) acetylating the 10-hydroxyl group in situ with an acetylating agent at 10°–40° C., (vii) deprotecting the 2', 7-hydroxyl groups with a mixture of mineral acid-polar solvent at 0°–10° C. (viii) isolating taxols A or B or C by chromatography over silica.

10 Claims, No Drawings

PROCESS FOR THE PRODUCTION OF TAXOL

FIELD OF THE INVENTION

This invention relates to a process for the production of taxols. More, particularly, this invention relates to a process for the isolation of xylosides of taxol A,B and C (taxol analogues A, B, C) from the stem bark of the Himalayan yew *Taxus wallichiana* and conversion of these isolated taxol analogues 7-xylosyl-10-deacetyl taxols A,B and C of the formula (1)

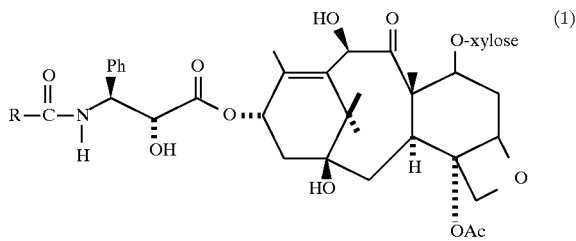

where R represents $C_6H_5$ (taxol analogue A or, xyloside A), or, $CH_3C=CH\ CH_3$ (taxol analogue B or, xyloside B), or, $C_5H_{11}$ (taxol analogue C or xyloside C) into 10-deacetyl taxols A, B, C (10-DAT-A, B, C) to be used as an intermediate for further conversion of the said isolated intermediates (10-DATS) into taxols A, B, C.

10-deacetyl taxols A,B,C have the formula (2) where R=$C_6H_5$ (10-de acetyl taxol A), or, $CH_3C=CH\ CH_3$ (10-deacetyl taxol B), or $C_5H_{11}$ (10-deacetyl taxol C).

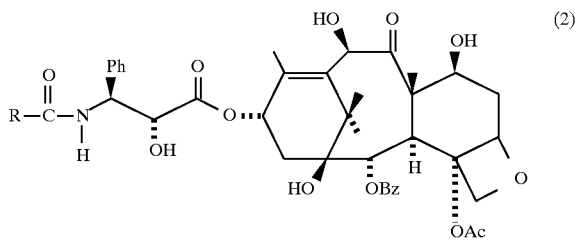

Taxols A, B, C have the formula (3) where R=$C_6H_5$ (taxol A), or $CH_3C=CHCH_3$ (taxol B) or $C_5H_{11}$ (taxol C).

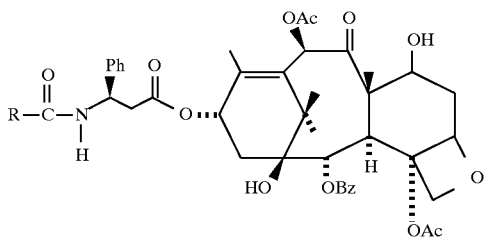

R = $C_6H_5$ (taxol A)
  = $CH_3C=CHCH_3$ (taxol B)
  = $C_5H_{11}$ (taxol C)

BACKGROUND OF THE INVENTION

Taxols A and B are also known in the literature as taxol and cephalomannine and taxol C has no other name [Mise en evidence nouveaux analogues du taxol extracts de *Taxus baccata*. V. Senilh, S. Blechert, M. Colin, D. Guenard, F. Picot, P. Potier and P. Varenne, *Journal of Natural products* 47, 131–137 (1984)]. Out of the three taxols A, B, C, only taxol A (=taxol) is used clinically for the treatments of ovarian and breast cancers. Various types of cancers have been treated with taxol A and the results in the treatments of ovarian and breast cancers are very promising. Taxol A (=taxol) has been approved by the Food and Drug Administration (FDA) of the United States for the treatments of ovarian and breast cancers.

Taxol B (=cephalomannine) has been isolated from the leaves, stems, roots of *Taxus wallichiana*; It is not clinically used. [Antileukemic alkaloids from *Taxus wallichiana*. R. W. Miller, R. G. Powell, C. R. Smith, Jr., E. Arnold, and J. Clardy, *Journal of Organic Chemistry* 46, 1469–1474 (1981)].

Taxol C has been isolated from the roots of *Taxus media* [Taxol analogues from the roots of *Taxus media*. L. Barboni, P. Garibaldi, E. Torregiani, G. Appendino, B. Gabetta and E. Bombardelli, *Phytochemistry* 36, 987–990 (1994)]. Taxol C has also been isolated from the cell cultures of *Taxus baccata* and it showed potent and selective cytotoxicity against cell lines of non-small-cell lung cancer, small cell lung cancer, colon cancer, CNS cancer and ovarian cancer; [New bioactive taxoids from cell cultures of *Taxus baccata*. W. Ma, G. L. Park, G. A. Gomez, M. H. Nieder, T. I. Adams, J. S. Aynsley, O. P. Sahai, R. J. Smith, R. W. Stahlhut, P. J. Hylands, F. Bitsch and C. Shackleton, *Journal of Natural Products* 57, 116–122 (1994)].

Taxol A, a highly oxygenated diterpenoid molecule and a potent anticancer drug was first isolated from the stem bark of *Taxus brevifolia*. Thereafter, it has also been isolated from other Taxus species including *Taxus wallichiana*. Taxol A, a structurally complicated and chemically labile molecule needed special and careful extraction and separation procedures for its isolation from plant materials. Unfortunately, most of the works are proprietary in nature and have not been published. The American workers have used alcohol to extract taxol from the stem bark of *T. brevifolia* and isolation of taxol from the alcoholic extract used sequential column chromatography over silica with methanol-chloroform mixture (2: 98) as the eluting solvent to yield a mixture of taxol A (=taxol) and Taxol B (cephalomannine). In one of the prior art process, Taxol A has been separated and isolated from the mixture containing taxol A and Taxol B with a yield of 0.01% either by repeated column chromatography over silica gel or by high performance liquid chromatography (HPLC). [M. C. Wani, H. I. Taylor, M. E. Wall, P. Coggan and A. T. Mc Phail. Plant antitumor agents VI: The isolation and structure of taxol, a novel antileukemic and antitumor agent from *Taxus brevifolia*. *Journal of the American Chemical Society* 93, 2325 (1971); and J. H. Cardellina: HPLC separation of taxol and cephalomannine, *Journal of liquid chromatography* 14, 659 (1991)].

According to another prior art process, Taxol A has been isolated from the stem bark of *Taxus wallichiana* with a yield of 0.02%. The isolation process involves extracting the stem bark with methanol, partitioning of the methanolic extract between water and chloroform and isolation of taxol A from the chloroform soluble fraction by column chromatography over silica gel. [S. K. Chattopadhyay, V. K. Tripathi, R. S. Thakur, R. P. Sharma and S. P. Jain. Isolation of taxol, 10-deacetyl baccatin III and (-) betuligenol from *Taxus baccata* 33B, 409 (1994)].

According to a prior art process, taxol analogues 7-xylosyl-10-deacetyl taxol A and B have been converted into taxol A (=taxol) and taxol B (cephalomannine) by K. V. Rao [Process for the preparation of taxol and deacetyl taxol, K. V. Rao, U.S. patent application Ser. No. 851469, 13 Mar. 1992].

The process for the preparation of taxols A or B involved reacting the analogue 7-xylosyl-10-deacetyl taxol A or B with periodate in methanol. Chloroform and sulphuric acid mixture at 20°–60° C. to give a dialdehyde product which was then treated with phenyl hydrazine in methanol-aqueous acetic acid mixture and heated at 50°–60° C. to degrade the dialdehyde into 10-deacetyl taxol A or B which was then isolated by column chromatography. The resultant 10-deacetyl taxol A or 10-deacetyl taxol B was then converted into taxol A (=taxol) or taxol B by reacting 10-deacetyl taxol A or B with an acetylating agent at 0°–100° C. to block the 2', and 7-hydroxyl groups, then acetylating the 10-hydroxyl group with an acetylating agent at 0°–100° C. followed by deprotecting 2' and 7-hydroxyl groups with a suitable deprotecting agent to taxol A or B.

The process for preparation of the intermediate product 10-deacetyl taxol A or B from 7-xylosyl-10-deacetyl taxol A or B, and conversion of 10-deacetyl taxol A into Taxol A (=taxol) as described by Rao suffers from major disadvantages which include low yield of the intermediate product 10-deacetyl taxol A, or B, eg. 0.5 g 7-xylosyl-10-deacetyl taxols A, or B yields 0.2 g 10-daecetyl taxol A or B; as well as low yield of the final product taxol A (=taxol) from its intermediates 10- deacetyl taxol A; eg. 0.5 g 10-deacetyl taxol A yields 0.3 g taxol A. No experimental procedure and yield are reported by Rao for conversion of the 10-deacetyl taxol B into taxol B (=cephalomannine).

The reasons for low yield of the intermediate products 10-deacetyl taxol A or B may be rationalized due to (i) carrying out the periodate oxidation of the 7-xylosyl-10-deacetyl taxol A or B in presence of mineral acid (although it is mentioned by Rao in his patent application that periodate oxidation can also be carried out under neutral condition in presence of excess sodium bicarbonate, the presence of excess dissolved sodium carbonate may lead to degradation of the side chain from dialdehyde leading to mixture of products) (ii) heating the periodate oxidation product with phenyl hydrazine in methanol-aqueous acetic acid mixture at 50°–60° C. to degrade the periodate oxidation product into 10-deacetyl taxol A or B.

The reasons for low yield of the final product taxol A (=taxol) from the intermediate product as described in Rao's process may be due to selection of improper protecting groups to block 2', 7-hydroxyl groups and non-optimization of reaction conditions such as duration of reaction time and temperature to carryout the protection of the groups.

Moreover, the processes for production of the intermediate product 10-deacetyl taxol C from the analogue 7-xylosyl-10-deacetyl taxol C and conversion of the above said intermediate product 10-deacetyl taxol C into taxol C have not been covered by Rao in his patent application.

SUMMARY OF THE INVENTION

In order to over come the drawbacks of the prior art processes, the applicants have developed a simple and practical process for production of taxols A, B, C; The process comprises (i) isolating the taxol analogues 7-xylosyl-10-deacetyl taxols A, B, C from the stem bark of *Taxus wallichiana* by an improved process developed by the applicants which involves extracting air, dried pulverized plant materials with alcohols at room temperature, evaporating the solvent to obtain a residue, stirring the resultant residue with water to a precipitate and isolating the taxol analogues 7-xylosyl-10-deacetyl taxol A, (taxol analogue A) 7-xylosyl-10-deacetyl taxol B (taxol analogue B) and 7-xylosyl-10-deacetyl taxol C (taxol analogue C) by flask chromatography over silica gel with yields 0.5% (for taxol analogue A), 0.2% (for taxol analogue B) and 0.0075% (for taxol analogue C), (ii) reacting the isolated taxol analogues A or B or C with periodates in a polar solvent at ambient temperature into dialdehyde (iii) reducing the resultant dialdehyde with borohydride in a polar solvent acetic acid mixture at 0°–40° C. into an acetal, (iv) degrading the acetal in a mixture of mineral acid and chlorinated solvent at 0°–40° C. to give the intermediate product 10-deacetyl taxol A or B or C, (v) protecting the 2', 7-hydroxyl groups of the intermediate 10-deacetyl taxol A or B or C with a suitable silane at 20°–40° C. for 20–40 hours, (vi) acetylating the free 10-hydroxyl group with an a cetylating agent at 10°–40° C. for 12–18 hours, (vii) deprotecting the silyl groups at 21, 7-positions in presence of mineral acid polar solvent mixture at 0°–10° C. to give the final product taxol A or B or C.

The yields of taxols A, B, C obtained by the process of the present invention has been compared with the corresponding yields reported earlier.

| Source | Taxol A | Taxol B | Taxol C |
| --- | --- | --- | --- |
| Stem bark | 0.001–0.02% | 0.006% | — |
| Needles | 0.002–0.01% | — | 0.035% |
| Previous art Rao's process | 0.012% | 0.012% | — |
| Present process | 0.25% | 0.25% | 0.25% |

DETAILED DESCRIPTION OF THE PROCESS

The objective of the present invention is to develop an improved process for isolation of xylosides of taxol A, B, C (taxol analogues A, B, C), 7-xylosyl-10-deacetyl taxol A, B, C of the formula (1) where R represents $C_6H_5$ (taxol analogue A or, xyloside A), or $CH_3$ C=CH $CH_3$ (taxol analogue B or xyloside B) or, $C_5H_{11}$ (taxol analogue C or xyloside C) from the stem bark of the Himalayan yew *Taxus wallichiana* with higher yields.

Another objective of the present invention is to develop a simple and cost effective process for conversion of these isolated taxol analogues 7-xylosyl-10-deacetyl taxols A, B, C into the intermediate product 10-deacetyl taxols A, B, C (10-DAT A, B, C) of the formula (2) where R represents $C_6H_5$ (10-deacetyl taxol A), or $CH_3$ C=CH $CH_3$ (10-deacetyl taxol B) or $C_5H_{11}$ (10-deacetyl taxol C) .

Still another objective of the present invention is to convert the intermediates 10-deacetyl taxol A, B, C into taxols A, B, C of the formula (3) where R represents $C_6H_5$ (taxol A) or $CH_3$ C=CH $CH_3$ (taxol B) or $C_5H_{11}$ (taxol C);

According to the first objective of the present invention, an improved process has been developed for isolation of the taxol analogues 7-xylosyl-10-deacetyl taxol A, B, C from the stem bark of *Taxus wallichiana* in which no solvent partitioning has been used to isolate the analogues. The improved isolation process comprises extracting air dried, pulverized plant materials with alcohols at room temperature, evaporating the solvent to obtain a residue, stirring the resultant residue with water to obtain a thick precipitate, isolating the analogues 7-xylosyl-10-deacetyl-taxol A, 7-xylosyl-10-deacetyl-taxol B and 7-xylosyl-10-deacetyl taxol C from the precipitate by flash chromatography over a bed of silica gel.

According to another objective of the present invention, a process has been developed for conversion of the isolated taxol analogues 7-xylosyl-10-deacetyl taxols A, B, C into the intermediate products 10-deacetyl taxols A, B, C (10-DAT A, B, C) of the formula (2) where R=$C_6H_5$ (10-DAT A) or $CH_3$ C=CH $CH_3$ (10-DAT B) or, $C_5H_{11}$ (10-DAT C)

which comprises dissolving the isolated analogue 7-xylosyl-10-deacetyl taxol A or B or C in a polar solvent, reacting the resultant solution with periodate for 20–40 hours at 20°–40° C. to cleave the diol system of the xyloside into dialdehyde, reducing the dialdehyde solution in a mixture of polar solvent—acetic acid mixture with borohydride at a temperature of 0°–40° C., acidifying the resultant acetal with a mineral acid in a chlorinated solvent for 2–4 hours at 0°–40° C. to 10-deacetyl taxol A or B or C.

According to still another objective of the present invention, a process has been developed for conversion of the intermediate 10-deacetyl taxols A, B, C into the final product taxols A, B and C of the formula (3) where R=C6H$_5$ (taxol A), or CH$_3$ C=CH CH$_3$ (taxol B), or C$_5$H$_{11}$ (taxol C) which comprises treating the resultant 10-deacetyl taxol A or B or C with silanes (more specifically chlorotriethyl silane, chlorotriisobutyl silane, chlorotrimethyl silane, chlortriisopropyl silane,) in a base at 10°–40° C. for 20–40 hours to protect the 2', 7-hydroxyl groups of 10-deacetyl taxol, acetylating the remaining free 10-hydroxyl group in situ with an acetylating agent at 10°–40° C. for 12–18 hours to a 2', 7-disylated taxol derivative and reacting the resultant derivative with mineral acid- polar solvent mixture at 0°–10° C. for 10–12 hours to deprotect the 2', 7-hydroxyl groups and isolating the taxols A or B or C by column chromatography over silica gel.

According to one embodiment of the invention, the polar solvent used in dissolving the taxol analogues 7-xylosyl-10-deacetyl taxols A, B, C, in the mixture of polar solvent and acetic acid to dissolve the dialdehyde for borohydride reduction and in the mixture of polar solvent and mineral acid mixture to deprotect the 2', 7-hydroxyl groups, may be selected from methanol, ethanol, propanol, butanol;

According to another embodiment of the invention, suitable periodates used in cleaving the diol system of the xyloside may be selected from sodium periodate, potassium periodate, periodic acid, para periodic acid.

According to another embodiment of the invention, the borohydrides used in reducing the dialdehyde into the acetal may be selected from sodium borohydride, potassium borohydride, lithim boro hydride, sodium cyano borohydride.

According to another embodiment of the invention, the mineral acid used in the mixture of chlorinated solvent for acidifying the acetal and also in the mixture of polar solvent to deprotect 2', 7-hydroxyl groups may be selected from hydrochloric acid, sulphuric acid, nitric acid, perchloric acid, hydrofluoric acid.

According to another embodiment of the present invention, the chlorinated solvent used in the mixture of mineral acid for acidifying the acetal may be selected from chloroform, dichloromethane, carbon tetrachloride.

According to another embodiment of the present invention, bases used in presence of silanes for protecting the 2', 7-hydroxyl groups and also with the acetylating agents for acetylation of 10-hydroxyl group may be selected from pyridine, triethylamine, dimethyl amino pyridine, piperidine, morpholine.

According to another embodiment of the present invention, the silanes used in protecting the 2', 7-hydroxyl groups of 10-deacetyl taxol A, B, C may be selected from chlorotriethyl silane, chlorotriisobutyl silane, chlorotriisopropyl silane, chlorotrimethyl silane.

According to another embodiment of the present invention, acetylating agents used to acetylate the 10-hydroxyl group may be selected from acetyl chloride, acetic anhydride, acetyl bromide.

According to another embodiment of the invention, the adsorbent used in flash chromatography for isolating taxol analogues 7-xylosyl-10-deacetyl taxols A, B, C and for purifying taxols A, B, C may be selected from silica gel, florosil, alumina.

The invention is described in details in the examples given below which are provided to illustrate the invention and therefore should not be construed to limit the scope of the invention.

EXAMPLE 1

Isolation of 7-xylosyl-10-deacetyl taxols A, B, C: The taxol analogues 7-xylosyl-10-deacetyl taxols A, B, C were isolated by an improved process developed by us in which no solvent partitioning step was used.

Air dried pulverized stem bark (1 kg) of *Taxus wallichiana* was extracted with methanol (3 liters x 3) for 72 hrs. at ambient temperature. The methanolic extract was concentrated to a residue. The residue was diluted with water and stirred mechanically to a thick precipitate. The precipitate was filtered, dried and the dried mass was dissolved in a minimum volume of ethylacetate—methanol mixture and subjected to flash chromatography through a bed of silica gel using ethyl acetate as the eluant. The eluant was changed to 2–5% methanol in ethylacetate. 2% methanol in ethylacetate gave 7-xylosyl-10-deacetyl taxol A (5 g), 4% methanol in ethylacetate gave 7-xylosyl-10-deacetyl taxol B (0.2 g) and 5% methanol in ethylacetate gave 7-xylosyl-10-deacetyl taxol C (75 mg).

EXAMPLE—2a

Production of 10-deacetyl taxol A. To a small reaction flask was added the analogue 7-xylosyl-10-deacetyl taxol A (100 mg), isolated by the process as described in example 1, in ethanol (20 ml); Sodium periodate (231 mg in 2 ml water) was added to the resulting alcoholic solution and the reaction mixture was stirred for 20–40 hours at 20°–40° C. The reaction mixture was diluted with water and extracted with ethyl acetate (2×30 ml). The ethylacetate phase was washed with water, dried over anhydrous sodium sulphate and concentrated in vacuo to a residue; The residue was dissolved in ethanol-acetic acid mixture and was treated with sodium borohydride (50 mg) at 0°–40° C. with stirring. The resultant reaction mixture was then diluted with chloroform (30 ml) and stirred with dil hydrochloric acid for 2–4 hours at 0°–40° C.; The chloroform layer was washed with water (2×30 ml), dried over anhydrous sodium sulphate and concentrated in vacuo to a resude. The resultant residue was triturated with hexane-chloroform mixture and filtered to give 10-deacetyl taxol A (70 mg). which was found to be identical with an authentic sample in all respects. [19-Hydroxybaccatin III, 10-deacetyl cephalomannine and 10-deacetyl taxol: new antitumor taxanes from *Taxus wallichiana*. J. L. McLaughlin, R. W. Miller, R. G. Powell and C. R. Smith, Jr. *Journal of Natural Products* 44, 312–319 (1981).]

EXAMPLE—2b

Production of 10-deacetyl taxol B. To a reaction flask was added the analogue 7-xylosyl-10-deacetyl-taxol B (100 mg), isolated by the process as described in example 1, in methanol (20 ml) and to it was added potassium periodate (230 mg in 2 ml water); The reaction mixture was stirred for 20–40 hours at 20°–40° C. and diluted with water and extracted with ethylacetate (2×30 ml); The ethylacetate phase was washed with water, dried over anhydrous sodium sulphate, and concentrated in vacuo to a residue; The residue was dissolved in methanol-acetic acid mixture and was treated with potassium borohydride (50 mg) at 0°–40° C. with stirring. The resultant reaction mixture was then diluted with dichloromethane (30 ml) and stirred with dil. sulphuric acid for 2–4 hours at 0°–40° C.; The dichloromethane layer was washed with water (2×30 ml), dried over anhydrous sodium sulphate and concentrated in vacuo to a residue. The resultant residue was triturated with hexane-dichloromethane mixture and filtered to get 10-deacetyl taxol B (70 mg) which was identical in all respect with an authentic sample [R. W. Miller et al. *J. Org. Chem.* 46, 1469–1474 (1981)].

EXAMPLE—2C

Production of 10-deacetyl taxol C The starting material, 7-xylosyl-10-deacetyl taxol C for the production of 10-deacetyl taxol C was isolated by a process as described in example 1. Following the process as described in example 2a or 2b, 7-xylosyl-10-deacetyl taxol C (100 mg) was converted into 10-deacetyl taxol C (70 mg), identical in all respects with an authentic sample [W. Ma et al. *J. Nat. Prod.* 57 116–122 (1994)].

EXAMPLE—3a

Production of taxol A from 10-deacetyl taxol A (10-DAT, A). 10-deacetyl taxol A (70 mg), prepared by the process of example 2a, was dissolved in pyridine (5 ml) and treated with chlorotriethyl silane (0.4 ml) at 10°–40° C. for 20–40 hours to protect the 2', 7-hydroxyl groups of 10-DAT, A. The reaction mixture was then treated in situ with acetic anhydride (0.2 ml) at 10°–40° C. for 12–18 hours. The reaction mixture was then quenched with crushed ice and left aside for half an hour and extracted with chloroform (30 ml). The chloroform layer was washed with water, dried over anhydrous sodium sulphate and concentrated to an oily residue; The resultant residue was triturated with hexane and solidifies. The solids were filtered and were treated with methanol-hydrochloric acid mixture at 0°–10° C. for 10–12 hours to complete the reaction. The reaction mixture was diluted with cold water and extracted with chloroform (30 ml); The chloroform layer was washed with water, dried over anhydrous sodium sulphate and concentrated in vaccuo to give a residue; The residue was purified by passing through a column of silica gel in chloroform; 2% m ethanol in chloroform eluted taxol A which was isolated as solids; The solids crystallized from hexane-ethylacetate mixture as needles to give taxol A (50 mg).

EXAMPLE—3b

Production of taxol B from 10-deacetyl taxol B (10-DAT, B). 10-Deacetyl taxol B (70 mg, prepared by the process of example 2b, was dissolved in triethylamine (5 ml) and treated with chlorotriisobutyl silane (0.4 ml) at 10°–40° C. for 20–40 hours to protect 2', 7-hydroxyl groups of 10-DAT, B. The reaction mixture was then treated in situ with acetyl chloride (0.3 ml) at 10°–40° C. for 12–18 hours; The reaction mixture was then treated with crushed ice and left aside for half an hour and extracted with dichloromethane (30 ml). The dichloromethane layer was washed with water, dried over anhydrous sodium sulphate and concentrated to on oily residue. The residue was triturated with hexane and solidifies. The solids were filtered and were treated with ethanol-sulphuric acid mixture at 0°–10° C. for 10–12 hours to complete the reaction. The reaction mixture was diluted with cold water and extracted with dichloromethane (30 ml). The dichloromethane layer was washed with water, dried over anhydrous sodium sulphate and concentrated in vacuo to give a residue. The residue was purified by passing through a column of florosil in dichloromethane; 3% methanol in dichloromethane eluted taxol B which was isolated as solids. It crystallized from methanol-water as needles to give taxol B (50 mg).

EXAMPLE—3c.

Production of taxol C from 10-deacetyl taxol C (10-DAT, C). Starting from 10-deacetyl taxol C (70 mg), prepared by the process as described in example 2c, taxol C (50 mg) was prepared following the process as described in example 3a or 3b. Taxol C was found to be identical in all respects with an authentic sample. [L. Barboni et al. *Phytochemistry* 36, 987–990 (1994)].

ADVANTAGES

1) Solvent partitioning step as reported in a published art [V. Senilh et al. *J. Nat. Prod.* 47, 131–137 (1984)] for isolation of taxol analogues 7-xylosyl-10-deacetyl taxols A, B, C was not utilized in the proecess of isolation of the said analogues of the present invention; Absence of solvent partitioning step lead to higher yields of the isolated analogues, 7-xylosyl-10-deacetyl taxol A, yield 0.5%; 7-xylosyl-10-deacetyl-taxol B, yield 0.02%; 7-xylosyl-10-deacetyl—taxol C, yield 0.0075%, compared to the reported yields [V. Senilh et al *J. Nat. Prod.* 47, 131 (1984)].

2) Compared to the previous art, diol of the xyloside system of the isolated analogues was cleaved into dialdehyde under non-acidic condition; No. acid is used in the periodate oxidation step.

3) Reduction of the dialdehyde by borohydride into acetal followed by degradation into 10-deacetyl taxols A, B, C (10-DAT, A, B, C) was achieved under mild condition 0°–40° leads to higher yields of the intermediate products (10-DAT, A, B, C).

4) Use of silanes leads to selective protection of 2', 7-hydroxyl groups of 10-deacetyl taxols A, B, C efficiently and also facilitates easy deportection of the groups under mild condition (0°–10° C.) leads to higher yield of taxols A, B, C.

5) So far, no process has been reported for production of taxols with this yields

| Source | Taxol A | Taxol B | Taxol C |
|---|---|---|---|
| Stem bark | 0.001–0.02% | 0.006% | — |
| Needles | 0.002–0.01% | — | 0.035% |
| Previous art | 0.012% | 0.012% | — |
| Present process | 0.25% | 0.25% | 0.25% |

We claim:

1. A process for the production of taxol A, B, C of the formula (3)

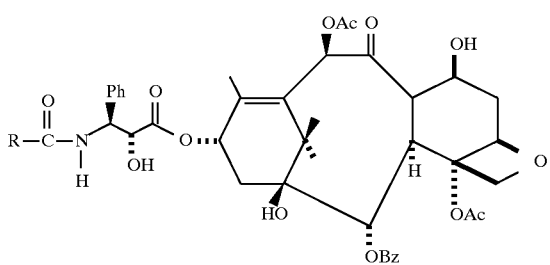

R = C₆H₅ (taxol A)
 = CH₃C=CH—CH₃ (taxol B)
 = C₅H₁₁ (taxol C)

Where R represents $C_6H_5$ (taxol A) or $CH_3 C=CH\ CH_3$ (taxol B) or, $C_5H_{11}$ (taxol C) which comprises isolating the taxol analogues 7'-xylosyl-10-deacetyl taxols A, B, C of the formula (1),

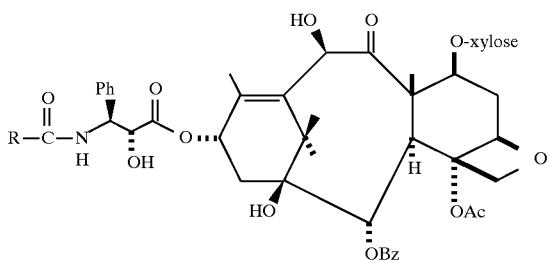

R = C₆H₅ (taxol analogue A)
 = CH₃C=CH CH₃ (taxol analogue B)
 = C₅H₁₁ (taxol analogue C)

where R represents $C_6H_5$ (taxol analogue A or xyloside A), or $CH_3\ C=CH\ CH_3$ (taxol analogue B or xyloside B) or $C_5H_{11}$ (taxol analogue C or xyloside C) from the stem bark of *Taxus wallichiana* (a) by extracting the air dried, pulverized stem bark with alcohols at ambient temperature, (b) evaporating the solvent to obtain a residue, (c) stirring the residue with water to obtain a thick precipitate, (d) isolating the analogues 7-xylosyl-10-deacetyl taxols A, B, C from the precipitate obtained by flash chromatography over a bed of silica, (e) dissolving the isolated analogue in polar solvent, (f) reacting the resultant solution with periodates at 20°–40° C. for 20–40 hours to cleave the diol system of the xyloside into dialdehyde, (g) reducing the dialdehyde solution with borohydrides at 0°–40° C. in a polar-solvent acetic acid mixture, (h) acidifying the resultant acetal with a mineral acid in a chlorinated solvent at 0°–40° C. for 2–4 hours to 10-deacetyl taxols A, B, C of the formula (2)

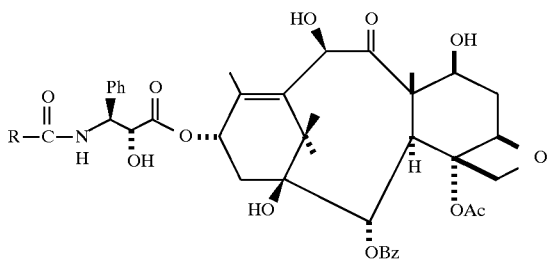

R = C₆H₅ (10-deacetyl taxol A)
 = CH₃C=CH CH₃ (10-deacetyl taxol B)
 = C₅H₁₁ (10-deacetyl taxol C)

where R represents $C_6H_5$ (10-deacetyl taxol A) or $CH_3C=CH\ CH_3$ (10-deacetyl taxol B) or $C_5H_{11}$ (10-deacetyl taxol C), (i) treating the resultant 10-deacetyl taxols A, B, C with specific silanes selected from (chlorotriethyl silane, chloro triisobutyl silane, chlorotriisopropyl silane, and chloro trimethyl silane) at a specific temperature of 10°–40° C. for a period of 20–40 hours to block the 2', 7-hydroxyl groups of lo-deacetyl taxols A, B, C; (j) acetylating the remaining free 10-hydroxyl group in situ with an acetylating agent at 10°–40° C. for 12–18 hours to a obtain solid residue; (k) reacting the resultant solids with a mixture of mineral acid-polar solvent at 0°–10° C. for 10–12 hours to deprotect the 2', 7-hydroxyl groups, and (1) isolating taxols A, B, C by column chromatography over silica.

2. A process as claimed in claim (1) wherein the polar solvents used in dissolving the taxol analogue 7-xylosyl-10-deacetyl taxols A, B, C, in the mixture of polar solvent and acetic acid to dissolve the dialdehyde for barohydride reduction, and in the mixture of polar solvent and mineral acid mixture to deprotect the 2', 7-hydroxyl groups, are selected from methanol, ethanol, propanol, butanol.

3. A process as claimed in claim 1, wherein the periodates used in cleaving the diol are selected from sodium periodate, potassium periodate, periodic acid, paraperiodic acid.

4. A process as claimed in claim 1 wherein the borohydrides used in reducing the dialdeyde into the acetal are selected from sodium borohydride, potassium borohydride, lithium borohydride, sodium cyanoborohydride.

5. A process as claimed in claim 1 wherein the mineral acid used in the mixture of chlorinated solvent for acidifying the acetal and also in the mixture of polar solvent to deprotect the 2', 7-hydroxyl groups are selected from hydrochloric acid, sulphuric acid, nitric acid, perchloric acid, hydrofluoric acid.

6. A process as claimed in claim 1 wherein the chlorinated solvent used in the mixture of mineral acid for acidifying the acetal are selected from chloroform, dichloromethane, carbon tetrachloride.

7. A process as claimed in claim 1 wherein the silanes used in protecting the 2', 7-hydroxyl groups of the 10-deacetyl taxols are selected from chlorotriethyl silane, chlorotriisobutyl silane, chlorotriisopropyl silane, chlorotrimethyl silane.

8. A process as claimed in claim 1 wherein the bases used in presence of silanes for protecting the 2', 7-hydroxyl groups and also with the acetylating agents for acetylation of 10-hydroxyl group are selected from pyridine, triethyl amine, dimethyl amino pyridine, piperidine.

9. A process as claimed in claim 1 wherein the acetylating agents used to acetylate the 10-hydroxyl group are selected from acetic anhydride, acetyl chloride, acetyl bromide.

10. A process as claimed in claims 1 wherein the adsorbent used in flash chromatography for isolating taxol analogues 7-xylosyl-10-deacetyl taxols A, B, C and for purifying taxols A, B, C are selected from silica gel, florosil, alumina.

* * * * *